United States Patent
De Manzanos Guinot et al.

(10) Patent No.: US 11,674,166 B2
(45) Date of Patent: Jun. 13, 2023

(54) SAMPLING OF MICROORGANISMS

(71) Applicant: FUNGIALERT LTD., Harpenden (GB)

(72) Inventors: Angela De Manzanos Guinot, Harpenden (GB); Kerry O'Donnelly Weaver, Harpenden (GB)

(73) Assignee: FUNGIALERT LTD., Harpenden (GB)

( * ) Notice: Subject to any disclaimer, the term of this patent is extended or adjusted under 35 U.S.C. 154(b) by 0 days.

(21) Appl. No.: 16/967,876

(22) PCT Filed: Feb. 8, 2019

(86) PCT No.: PCT/EP2019/053155
§ 371 (c)(1),
(2) Date: Aug. 6, 2020

(87) PCT Pub. No.: WO2019/154997
PCT Pub. Date: Aug. 15, 2019

(65) Prior Publication Data
US 2021/0047674 A1   Feb. 18, 2021

(30) Foreign Application Priority Data

Feb. 8, 2018   (GB) .................................... 1802060

(51) Int. Cl.
*C12Q 1/24*   (2006.01)
*C12Q 1/04*   (2006.01)
*G01N 1/02*   (2006.01)

(52) U.S. Cl.
CPC ............... *C12Q 1/24* (2013.01); *C12Q 1/045* (2013.01); *G01N 1/02* (2013.01)

(58) Field of Classification Search
CPC ............. C12Q 1/24; C12Q 1/045; G01N 1/02
See application file for complete search history.

(56) References Cited

U.S. PATENT DOCUMENTS

| 4,054,491 A | 10/1977 | Lindgren |
| 10,767,209 B2 * | 9/2020 | Weaver ..................... C12Q 1/04 |
| 2013/0334042 A1 | 12/2013 | Grieve |

FOREIGN PATENT DOCUMENTS

| WO | 94/08042 | 4/1994 | |
| WO | 99/10472 | 3/1999 | |
| WO | 99/10539 | 3/1999 | |
| WO | WO-9910472 A1 * | 3/1999 | ............... C12Q 1/24 |
| WO | 03/046136 | 6/2003 | |
| WO | WO-2011139263 A1 * | 11/2011 | ............ C12M 23/22 |
| WO | 2016/097726 | 6/2016 | |
| WO | WO-2016097726 A1 * | 6/2016 | ............ C12M 25/02 |
| WO | 2017/207756 | 12/2017 | |
| WO | WO-2017207756 A1 * | 12/2017 | ............... C12Q 1/04 |

OTHER PUBLICATIONS

Yang et al., 2015 (Relation between chemotaxis and consumption of amino acids in bacteria; Molecular Microbiology 96(6): 1272-1282) (Year: 2015).*
"Identification of *Phytophthora* spp. Isolated from plants and soil samples on strawberry plantations in Poland." Journal of Plant Diseases and Protection, vol. 123, No. 1. Feb. 1, 2016, pp. 29-36.
International Search Report for International Application PCT/EP2019/053155, dated May 3, 2019.
UK Search Report Under Section 17 and 18(3) for Application No. GB1802060.2, dated Jul. 30, 2018.

* cited by examiner

*Primary Examiner* — Mary Maille Lyons
(74) *Attorney, Agent, or Firm* — The Dobrusin Law Firm, P.C.; Daniela M. Thompson-Walters

(57) ABSTRACT

A device for sampling microorganisms comprising a hollow probe that can be inserted into a growth substrate or water system, the probe containing a growth medium for microorganisms wherein the growth medium contains a chemoattractant particularly a plant pathogen chemoattractant wherein the growth medium is specific for the microorganism/microorganisms which a grower wishes to know if they are present in the growth substrate or water system.

17 Claims, 1 Drawing Sheet

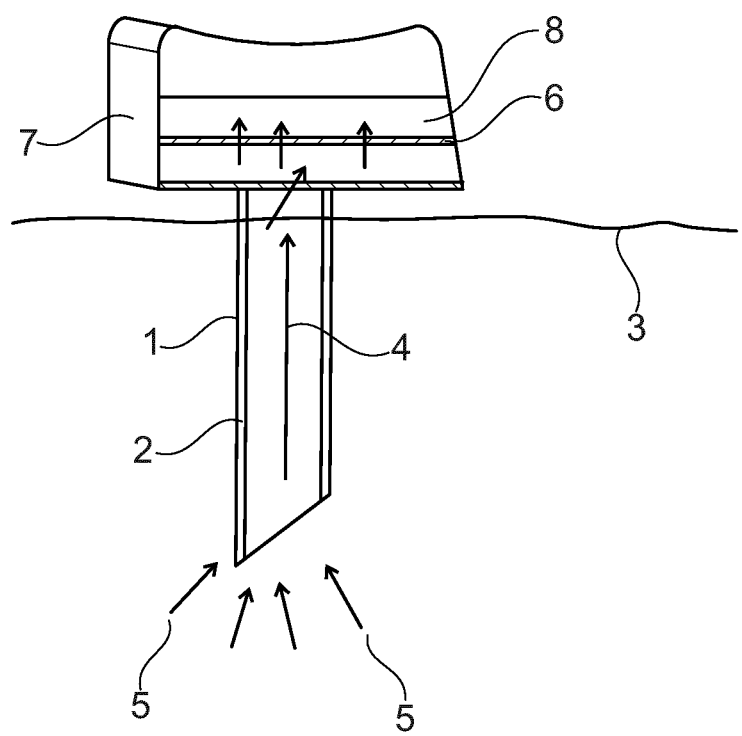

SAMPLING OF MICROORGANISMS

FIELD

The present teachings relate to a device for sampling microorganisms. The sampling device may comprise a hollow probe which can be inserted into a growth substrate or water system, the probe containing a growth medium for microorganisms.

BACKGROUND

The present invention relates to the collection of samples from an agricultural or horticultural growth substrate such as soil and/or water to enable the detection of microorganisms therein. The microorganisms with which the invention is concerned include pests and other microorganisms (such as fungi, oomycetes, bacteria and nematodes) which exist in an abundance in a growth substrate. In particular it relates to the collection of plant pathogens from a growth substrate and more particularly to the in situ collection of samples which can be analysed for the presence of pests and organisms that can cause disease in plants in the field or areas where products are being grown on a commercial basis or in their natural environment. The invention is also concerned with equipment that may be used in such a collection.

The invention helps in the early detection of microorganisms that have the potential to cause damage to plants and can also be used to detect the presence of microorganisms such as photosynthetic bacteria (such as *Rhodopseudomonas palustris* and *Rhodobacter sphaeroides*), lacto bacteria (such as *Lactobacillus plantarum* and *casei*, and *Streptococcus*), yeasts (such as *Saccharomyces* spp.), actinomycetes (such as *Streptomyces* spp.), $N_2$ fixing bacteria (such as *Rhizobium, Bradyrhizobium, Ensifer* and *Mesorhizobiu*), Mycorrhizae and phosphate solubilising microorganisms (such as bacteria (*Bacillus*) and fungi (*Aspergillus, Penicillium* spp.)), plant growth-promoting rhizobacteria, and probiotics for plants (such as *Pseudomonas*). These microorganisms can be beneficial to the health of plants and the invention helps to provide information to the grower concerning the need or otherwise to provide materials to enhance the well being of the plant in question.

Loss of plant yield due to plant disease from microorganisms including pathogens such as fungi, oomycetes, bacteria, nematodes and damaging insects is a global concern, not only in agriculture and horticulture but also in forestation, garden centres, private gardens and ornamental plants. Many valuable crops and ornamental plants are very susceptible to disease and would have difficulty surviving in nature without human intervention. Loss of products reared in water such as fish farms in lakes is also of concern.

Cultivated plants are often more susceptible to disease than their wild relatives because large numbers of the same species or variety (which have a uniform genetic background), are grown closely together, sometimes over many thousands of square kilometres. Disease caused by pathogenic organisms may spread rapidly under these conditions. For example, *Phytophthora*, a plant pathogen that generates spores that attack the roots and stems of a range of plants, vegetable and fruits, is of particular concern to growers as it can contaminate water supplies and can also stay undetected in plant debris and soil for many years. It is estimated that *Phytophthora*, known as the "Plant Destroyer of the $21^{st}$ Century", alone causes a $2-7 billion loss per crop per year worldwide (Roy et al, 2012 Review of Plant Pathology, Vol 6).

Numerous methods exist to detect plant disease. For example in the detection of plant pathogenic species, farmers typically use consultant agronomists who take a sample of soil or plant material, for example the leaf or root, and analyse the sample for the presence of plant pathogens. Analysis is conducted externally at a location remote from the sampling using laboratory tests. Such laboratory tests can include molecular techniques such as ELISA, PCR (PCR and real-time PCR), immunofluorescence (IF), flow cytometry, fluorescence in situ hybridization (FISH), and DNA microarrays. There are several problems with external laboratory testing of soil or plant material samples, for example it is necessary to extract the microorganism from the sample, furthermore the sampling selects only a small sample and may not necessarily reflect the true condition of the soil. Additionally, some of these techniques are not able to differentiate between dead or alive microbiological material.

In some cases, the level of pathogenic organisms in the selected samples of the soil may be too low for detection, therefore in sampling an isolated area of soil the detected level of plant pathogen will be ineffective despite the presence of damaging amounts of the pathogen. External laboratory analysis requires transportation of samples away from the sampling site to a laboratory where the samples need to be purified to be ready for analysis and then analysed. This causes a delay in providing the result of the analysis. Any delay in detecting an organism which can cause disease in a plant, such as a plant pathogen, can lead to a spread of the disease and a greater number of plants being affected.

Samples can also be tested for the presence of pathogenic organisms using on-site lateral flow devices. Such devices require the farmer to take a sample from a plant, for example a leaf. The method extracts nucleic acids or proteins from the plant sample and the presence of a plant pathogen can be detected. However, each plant sample is representative only for the plant being tested. Each sample is therefore not representative of the entire plant growth area. Further, a plant sample that tests positive for a plant pathogen indicates the plant has already been affected by the pathogen and this may be too late to prevent damage due to the pathogen and also too late to prevent spread of the plant pathogen to surrounding plants.

Early detection of threats to plant health and disease such as pests and plant diseases, caused by microorganisms, such as fungi, oomycetes, bacteria, and nematodes could facilitate the control of disease through proper crop management strategies such as vector control through pesticide applications, fungicide applications and disease-specific chemical applications and bio-controls. Additionally early detection in nurseries would enable the production and supply of disease free plants. Furthermore early detection in water systems such as irrigation systems and aquifers would help determine the safety of using the water for agricultural and horticultural purposes. There is therefore a need to provide an efficient and simple method and device for collecting and detecting these undesirable pathogenic species from soil or water that can be utilised at the site of plant growth or potential plant growth or water supply to provide the microorganism or pathogenic species substantially free from the soil, water or plant material from which it would require separation. This then permits subsequent analysis.

In our PCT publications WO 2016/097726 and WO 2017/207756 describe devices for detecting plant pathogenic microorganisms in soil or water particularly for detecting prior to the pathogen impacting the plant and this application contains a list of pathogens and this invention is inter alia applicable to the pathogens listed in that application.

United States Patent Publication 2013/0334042 describes the detection of airborne pathogen spores in situ in fields however this procedure requires considerable time for analysis to detect the pathogen. Furthermore, the technique cannot be used to detect pathogenic microorganisms in growth substrates or water.

U.S. Pat. No. 4,054,491 discloses a microorganism testing device in which a sample is sucked into a pipette like chamber where it is brought into contact with a growth medium.

WO 03/046136 relates to a single tube screen for the detection of microorganisms comprising a culture medium disposed within a chamber.

Some pathogenic species, such as fungi, oomycetes and bacteria, may exist and be dormant for long periods of time in growth substrates or water and they can be activated by environmental changes such as rain, heat or other weather related issues. Once activated they can come into contact with vegetation, typically the roots of vegetation where they can enter into the vegetation and cause considerable damage to the particular crop. The vegetation may comprise the entire range of agricultural and horticultural crops, such as fruit crops such as orchards and vineyards, flower production, garden centres and ornamental gardens plants and trees growing in their natural environment such as in forests. This invention may be used for early collection and quicker analysis of organisms which cause plant diseases, such as pathogenic microorganisms (fungi, oomycetes and bacteria), in nurseries where plants are grown for supply enabling greater confidence that the young plants are disease free. Pathogenic organisms may also exist in water systems such as water used for irrigation, aquifers, water gardens, reservoirs, tanks and lakes providing fish farms.

PCT Publication WO 94/08042 describes *Phytophthora cinnamomi* as one of the most important plant pathogens found throughout the tropical and temperate zones and this invention is particularly useful with *Phytophthora* type pathogens and describes using a solid dipstick coated with chemo attractants to detect the pathogen in a medium in which the organism is mobile and requires forming a solution of the sample into which the solid dipstick is placed.

SUMMARY

The present teachings relate to a sampling device comprising: a) a probe which is hollow and that can be inserted into a growth substrate or a water system; and b) a growth medium for microorganisms, wherein the growth medium is contained in the probe; and wherein the growth medium contains a chemoattractant which is a plant pathogen chemoattractant.

BRIEF DESCRIPTION OF DRAWINGS

FIG. 1 illustrates a sampling device according to the present teachings.

DETAILED DESCRIPTION

In one embodiment the present invention relates to the measurement of the health of growth substrates in relation to the presence of microorganisms in the growth substrate such as soil particularly prior to planting of crops or during the growing season. The presence of microorganisms whether they be pathogenic or beneficial to the particular crop has a significant impact on plant growth and crop yield. Knowledge of the soil and the microorganisms within it can influence the nature of the crop suitable for growth in the soil in question and/or can indicate the nature and amount of remedial chemicals that should be used to destroy undesirable pathogens and thereby improve plant growth and crop yield.

Typically, soil analyses involve the grower providing samples of soil, typically about 500 grams to 1 kilogram of soil to an analytical laboratory together with a list of the microorganism they wish to know if they are present in the sample. The analysis of the sample then involves purification in order to obtain a sufficient amount of the microorganism of sufficiently pure material for characterisation and searching for the microorganisms of concern, which again is time consuming and expensive. The identify of the microorganisms present can be determined from the purified material using molecular biology techniques. This process of obtaining a sample from the soil that can be used for identification of the microorganism and subsequent analysis can be time consuming and expensive. Typically, the overall detection process can take up to 3 or 4 weeks. Furthermore, with some of the molecular biology techniques currently used, dead microbiological material present in the soil can also trigger a positive result, giving misleading information.

The present invention provides technology that can collect the microorganisms from the growth substrate or water system in situ so avoiding the need for the provision of samples of growth substrate or water. The invention further provides that the microorganism should grow following its collection to increase concentration to enable detection. The invention further provides the in laboratory treatment of the sample to obtain material for microorganism detection. The invention therefore provides a faster, cheaper and more reliable process for the identification of microorganisms in growth substrates or water systems.

The invention therefore provides the collection of microorganisms directly from a growth substrate or water system into a container which can be sent for direct identification of the microorganisms; in a preferred embodiment the container contains a growth medium for the microorganism to grow.

Accordingly the invention provides a sampling device comprising a hollow probe that can be inserted into a growth substrate or water system wherein the probe contains a growth medium for microorganisms.

The probe may act as a container for the microorganism or it may extend from a container at the end remote from the end that is inserted in the growth substrate or water and provided with a releasable closure whereby the microorganisms can migrate into and be stored in the container.

We have found that when such a probe is placed in the growth substrate or water system microorganisms in the soil will migrate into the probe where they can be retained for analysis.

The growth medium may be specific for the microorganism which the grower wishes to know if it is present in the growth substrate or water system. Alternatively one or more growth medium may be used to enable a plurality of microorganisms to be collected.

Accordingly the use of the device of this invention enables microorganisms to be obtained and collected directly from a growth substrate or water system and grown so that the device containing the one or more microorganisms can be taken to a laboratory for detection of the microorganisms present without the need for further purification or treatment of the sample. This is particularly useful for pre-screening a field before taking rotational decisions about which crops to plant where.

In a preferred embodiment, the invention further provides the use of a device comprising a hollow probe linked to a container with a releasable cover, the probe and the container both containing a growth medium for microorganisms for obtaining samples of microorganisms from a growth substrate and/or water or a water system for subsequent detection of the microorganism.

The invention further provides a process for the detection of the presence of microorganisms in a growth substrate comprising placing the probe according to this invention in the growth substrate or a water system in order to collect microorganisms and transporting the probe and optional container containing the microorganisms to a laboratory for analysis to determine the nature of the microorganisms present. The result of the analysis can then be communicated back to the grower to provide the information required to treat or otherwise the growth substrate or water in order to improve the growth and yield of their crops.

The term growth substrate includes any natural and synthetic substrates in which plants may be grown and includes soil, coir, peat, sand, water and mixtures thereof.

As used herein, the term "growth medium" includes any substance which encourages the growth of the microorganism to be detected which may be a plant disease or disease causing species or a plant damaging pest, as well as beneficial microorganisms. The growth media or a component of the growth media will be selected according to the microorganism of interest. The growth medium can incorporate amino acids or alcohols, plant extract or specific plant compounds such as phytohormones, plant proteins or plant signalling compounds, sugars, organic acids, phenolics or other proteins such as casein, pectin and any derivatives of these may also be used as attractants. The choice of growth medium will depend upon the microorganism such as the disease or disease causing organism that is to be detected.

The growth medium attracts the microorganisms from the growth substrate or water system into the hollow probe and then into the container if one is used. The growth medium for the microorganism is provided in a manner that both encourages growth of the microorganism and directs the microorganism into the probe and optionally into the container. For example the hollow probe, which may be a probe, a tube or a needle may be designed to be placed within the growth substrate or water system and it may be connected at the other end of the probe, tube or needle to a compartment which provides a container where the microorganism extracted from the growth substrate or water system can be stored. At least part of the inner surface of the hollow probe, tube or needle may be coated with the growth medium such as a solid medium and the pattern of the coating may be such that it encourages the microorganism to move up the probe and into the container where such a container compartment is used. The growth medium can encourage the microorganism to move up the probe and into the container compartment and to grow as it moves up the probe. The microorganism therefore grows on the medium.

For example, where the device is configured so that in use the container compartment is positioned at the top end of the hollow probe, tube or needle and the bottom end of the hollow probe, tube or needle is configured to be within the growth substrate or water system if the growth medium is provided as a vertical strip on the inner surface of the hollow probe, tube or needle it will encourage the microorganism to move upwards along the strip and into the container compartment.

The growth medium employed will depend upon the nature of the microorganism whose presence in the growth substrate or water system is to be determined. The growth medium may also contain ingredients such as fungicides or antibacterial agents which can destroy or reduce the amount of microorganisms entering the device and which are not the microorganism which is to be detected.

The growth medium used in this invention will attract specific microorganism(s) which will then travel through the hollow, probe, tube or needle into the container. The growth medium aids growth of the microorganism(s) and can have many different compositions, depending on the microorganism(s) being collected. Examples of suitable growth media are described in Jeffers and Martin (Plant Disease, 1986, Vol. 80 No. 11) and Guo and Ko (*Applied Environmental Microbiology*, July 1993, Vol. 59, No. 7, p 2323-2325).

In one embodiment the growth medium comprises antibiotics and/or nutrients. The presence of antibiotics can prevent growth of undesirable bacteria. In another embodiment the growth medium comprises pesticides or fungicides and the presence of antibiotics, pesticides and/or fungicides allows the growth of the microorganism of interest and prevents the growth of microorganism not of interest, for example other fungi and bacteria that may have entered the hollow probe, tube or needle. In one embodiment the growth medium comprises nitrobenzenes or isoflavonoids. The growth medium can contain any combination of agar, nutrients, alcohols, amino acids, fungicides, pesticides, antibiotics, nitrobenzenes, plant extracts and/or isoflavonoids.

If a container compartment is used, the growth medium in the hollow tube, probe or needle may be at a lower concentration than the growth medium in the container as this can encourage the microorganism to move into the container. The growth medium may additionally comprise a buffer which maintains the pH of the medium in the hollow tube, probe or needle. The growth medium in the container may also comprise a buffer which may be at a lower concentration than the buffer in the medium in the hollow tube, probe or needle. The lower concentration of buffer in the container means that the pH level of the medium in the container can be altered. In one embodiment the growth medium in the hollow tube, probe or needle comprises a buffer and the growth medium in the container does not comprise a buffer. The absence of buffer in the container means that the pH level of the medium can be altered.

In one embodiment the growth media are agar culture media.

As indicated in a preferred embodiment where a container compartment is used the container also includes a growth medium for the microorganism which enables the organism to multiply to provide a high enough concentration of the microorganism in the container for subsequent analysis. The time required for multiplication varies according to the nature of the organism but we have found that using the techniques of this invention it can be accomplished more quickly than with currently existing techniques, and this invention offers a simple in-situ collection device, that does not require further sample manipulation.

The invention is applicable to any microorganisms, at any stage in their lifecycle, for example, it is applicable to any type of spore produced by a disease causing organism, such as fungi, oomcyete, and bacteria, including bacterial spores and motile spores such as zoospores.

In one embodiment the present invention is applicable to the collection of any plant pathogens including at least one species of *Phytophthora*. "*Phytophthora*" includes all the species of the genus *Phytophthora*.

Other pathogens to which the invention may be applied include *Magnaporthe, Botrytis, Cochiliobolus, Puccinia, Gymnosporangium, Hemileia*, and all the species of the genus *Fusarium*.

Further pathogenic organisms to which the invention may be applied include *Gibberella, Blumeria, Mycosphaerella, Colletotrichum, Sphacelotheca, Sporisorium, Ustilaginoidea, Ustilago, Melampsora, Pythium*, including all the species of the *Pythium, Achyla, Aphanomyces, Albugo, Wilsoniana, Basidiophora, Bremia, Alternaria, Pseudopezicula, Cercospora, Elsinoë, Sphaceloma, Armillaria mellea, Rhizomorpha, Diplocarpon, Marssonia, Erysiphe, Plasmopara, Guignardia, Colletotrichum, Glomerella, Stemphylium, Pleospora, Ulocladium, Stemphylium, Thielaviopsis, Chalara, Pseudocercospora, Macrophomina, Macrophoma, Vaccinium, Pyrenochaeta, Didymella, Stemphylium, Botryotinia, Fulvia, Mycovellosiella, Cladosporium, Passalora, Phom, Oidiopsis, Leveillula, Cochliobolus, Curvularia, Rhizoctonia, Bipolaris, Waitea, Thanatephorus, Corticium, Rhizopus, Septoria, Geotrichum, Galactomyces, Sclerotinia, Sclerotium, Athelia, Corynespora, Verticillium, Acremonium, Cephalosporium, Lasiodiplodia, Botryodiplodia, Physoderma, Physalospora, Diplodia, Botryosphaeria. Stenocarpella, Sclerophthora. Sclerospora, Peronosclerospora, Nigrospora, Khuskia, Trichoderma, Hypocrea, Phyllachora, Botryotinia, Cunninghamella, Doratomyces, Cephalotrichum, Gonatobotrys, Pithomyces, Scopulariopsis, Claviceps, Sphacelia, Phyllosticta, Mycosphaerella, Gloeocercospora, Kabatiella, Exserohilum, Helminthosporium, Setosphaeria, Hyalothyridium, Ascochyta, Bipolaris, Epicoccum, Drechslera, Graphium, Leptosphaeria, Ophiosphaerella, Scolecosporiella, Paraphaeosphaeria, Phoma, Septoria, Penicillium, Phaeocytostroma, Sphaerulina, Dictochaeta, Microdochium, Mucor, Mariannaea, Periconia, Physopella, Rhopographus, Spicaria, Angiopsora, Nectria Phomopsis, Spicaria, Selenophoma, Gaeumannomyces, Myrothecium, Monascus, Bremiella, Pseudoperonospora, Rhizophydium, Synchytrium, Olpidium, Ligniera, Plasmidiophora, Polymixia, Sorodiscus, Sorosphaera, Spongospora. Tetramyxa* and *Aspergillus*.

The growth medium may be provided on a carrier upon which it may be absorbed. In a preferred embodiment a gelling agent is added to the growth medium by which it adheres to the inside of the hollow tube, probe or needle of the device upon which the disease forming species colonises and travels upwards. The film or membrane may be provided on the interior surface of the hollow tube, probe or needle which extends into the growth substrate or water and provides a delivery mechanism for the microorganism usually a disease causing organism from the growth substrate or water system. In one embodiment, the growth medium is provided in a manner that enables at least some of it to leach out from the hollow tube, probe or needle into the growth substrate or water system, for example the growth medium may be a mixture of two or more materials each having a different solubility or miscibility with the growth substrate or water system. In this way some growth medium can be leached out into the growth substrate or water system to attract the disease causing organism and some will remain in the hollow tube, probe or needle and so direct the disease causing organism into the hollow tube, probe or needle.

The growth medium composition can perform the triple function that firstly it attracts the microorganism into the device, secondly it directs the microorganism up the hollow tube maybe into the container and thirdly it can cause the microorganism to grow as it moves up the tube, probe and needle and possibly within the container. In a further preferred embodiment the growth medium can contain ingredients which perform a fourth function of destroying or reducing the amount of microorganisms that are present other than those to be detected and so limiting their ability to enter the container and interfering with the subsequent analysis.

Where plant pathogens are to be collected the growth medium will typically be specific for the plant disease causing species. The growth medium may be specific for one type of disease causing species such as a particular plant pathogen or alternatively it may attract more than one type of plant disease causing microorganism. In one embodiment, a plant pathogen growth medium is used that is specific for several different plant pathogens. Alternatively the different plant pathogen growth medium used may be specific for different plant pathogens.

The hollow tube, probe or needle should be robust and resistant to corrosion in the growth substrate. Plastic probes or tubes being particularly useful. The growth medium should be provided in an amount such that if, as is preferred some of the growth medium has leached out from the tube or probe into the growth substrate the growth medium remaining in the tube or probe is in a concentration gradient wherein the growth medium is present at a higher concentration nearer to the container than at the end of the means that is placed in the growth substrate. In other words, the concentration is lower at the end of the delivery means that will be in contact with the growth substrate when in use than at the other end. The other end may deliver the microorganism to the container when used and this concentration gradient may be provided initially or it may be formed in situ during operation of the collection system. Although not essential such a gradient can assist in causing the microorganism to be carried up the hollow tube, probe or needle and maybe into the container.

The one or more hollow tubes, probes, or needles may be pointed to help with insertion into soil and may be of an internal diameter such that as the microorganism grows by contact with the growth medium it can pass upwardly along the bore of the probe(s), tube(s) or needle(s). Alternatively the growth medium may be held inside the hollow tube, probe or needle by a membrane which can release at least some of growth medium into the growth substrate or water. The disease causing species are attracted by the growth medium into and up the hollow tube, probe or needle until it reaches the container. Where several hollow probes, tubes or needles are employed they are preferably channelled to feed into a single container although each may have its own container.

The size and shape including the cross section of the hollow tube, probe or needle can be selected according to the location in which the device is to be used and also the nature of the microorganism to be detected. The thickness location and concentration of the coating of the growth medium on the inner surface of the hollow tube, probe or needle may also be selected according to the nature of the microorganism to be collected. We have found that hollow tubes, probes or needles of from 4 to 10 cm long with a cross sectional area of from 0.5 to 5 sq cm are particularly useful and that coatings of the growth medium of thickness from 0.1 to 1 cm particularly 0.2 to 0.5 cm are very effective.

When used in a growth substrate or a water system the growth medium should not be inactivated by the growth substrate or water system and materials contained therein. It should also be stable in the temperature ranges experienced in the particular environment in which it is used. When used in a growth substrate the growth medium should have some solubility in the moisture contained in the growth substrate and when used in water it should be selected to have the required solubility in water under the conditions in which it is used. Where the growth medium is provided as a coating on the internal surface of a hollow probe, tube or needle such as being held in a gel or being absorbed on a carrier such as a film or membrane attached to the inner surface of the hollow probe, tube or needle it may be releasable into the growth substrate to attract the microorganism whilst also being retained on the inner surface of the tube or probe to direct the microorganism to the container. This may be accomplished by providing the growth medium as two or more layers on the inner surface of the hollow tube, probe or needle. It is however important that sufficient growth medium remains on the inner surface of the hollow tube, probe or needle.

We have found that amino acids and/or $C_1$ to $C_4$ monohydric alcohols and mixtures thereof as well as divalent metals particularly calcium are particularly useful growth medium and they also act as chemoattractants particularly for the spores of *Phytophthora* and *Pythium*. We have also found that they may conveniently be provided on a membrane such as a nylon or nitro cellulose membrane or in a gel such as agar.

In operation of this invention with disease causing microorganisms once active the disease causing organism within the growth substrate will be attracted by the growth medium and will move or grow towards the growth medium which is provided in a manner that then directs the microorganism into the hollow tube, probe or needle and in a preferred embodiment up the tube and into the container. In this way the disease causing organism can be isolated from and collected from the growth substrate or water system and passes into the container. The probe and/or container can then be sent to the laboratory for analysis which can be performed sufficiently quickly in many instances to obtain species specific results before the organism has significant interaction with the particular vegetation allowing remedial action to be taken before the disease causing organism causes significant damage to the vegetation.

The system of this invention can be used for the collection of any particular microorganism. For example, in one embodiment it may comprise a filter system designed to permit the passage of the microorganism in question and to exclude other materials perhaps including other microorganisms. In one embodiment of the invention a growth medium for a disease causing organism is also included in the container of the device to ensure that the disease causing organism is not only attracted to the hollow tube, probe or needle but is attracted to flow up the hollow tube, probe or needle and into the container. In this instance the growth medium can be provided in gradually increasing amounts within the hollow tube, probe or needle and also within the container to ensure that the organism is directed into the container.

Although optional, in one embodiment the collection material employed in the invention comprises a filter. When a filter is used it selectively allows the microorganism being collected to reach the container and prevents species of different shapes and sizes from reaching the medium in the container. By using a selective filter in combination with growth medium for a specific microorganisms of interest the device can be used to collect a microorganisms of interest.

Alternatively and in a preferred embodiment there is chemical or biological filtration by the provision of antibiotics and antifungals within the growth medium provided on the inner surface of the tube, probe or needle and optionally within the collection material.

This invention as described may be implemented in agriculture and horticulture by placing one or more of the devices of this invention in the growth substrate adjacent to materials being grown therein. The optimum distance between devices in, for example, a field, will depend on the nature of the crop, the type of growth substrate, the prevailing climate etc. These can all be determined by trial and error although preliminary results suggest groups of devices such as that from 10 to 20 devices per hectare will be sufficient. In another embodiment the invention may be employed in freshly tilled growth substrate or available water systems to obtain samples for subsequent analysis to determine their suitability for public consumption or use and use in agriculture and horticulture and the need for addition of material such as fertilizers, pesticides, insecticides, fungicides and the like. The invention therefore further provides an array of devices of this invention distributed across a field or a water system. In a further embodiment one or more devices of this invention may be placed in water systems in order to aid assessment of the purity of the water system.

Once the particular microorganism has been collected in the device of the present invention the device containing the microorganism can be sent to the laboratory for analysis. Where a container is used the container is preferably provided with a releasable cap which can be removed and the contents of the container subject to microbiological analysis such as LAMP, Taqman, PCR and DNA barcoding analysis. The invention allows simple and rapid testing of the health of growth substrates before planting therein and can be used to monitor disease during the growing season to provide and guide spraying practices. It can also be used to monitor disease in water systems such as irrigation systems and aquifer or hydroponic crops additionally it can be used to monitor the efficiency of chemical treatments.

The invention is illustrated by reference to the accompanying FIGURE which shows a device of the present invention ready for use FIG. 1 shows a hollow probe or tube (1) carrying internally a layer (2) of an growth medium for the microorganism of interest. The probe or tube passes down into growth substrate or water system the surface of which is shown at (3). Some of the growth medium leaches out into the growth substrate to attract the microorganism (5) which is directed into the hollow tube as indicated by the arrows and up the tube as shown by arrow (4). The microorganism grows during contact with the growth medium and then passes into the container (7) which contains a growth medium (6). The sample of the microorganism (8) is stored within the container and the device may be removed from the growth substrate or water system and sent to a laboratory where the analysis for the microorganism may be performed. Once the microorganism has been removed from the device it may be cleaned and returned to the grower for reuse.

The invention is illustrated by reference to the following Example.

Example 1: Sampling and subsequent analysis of microorganisms from soil in carrot fields using a sampling device illustrated in the FIGURE.

Several sampling devices were designed to be specific for the collection of oomycetal species were placed in the soil. The hollow probe and container contained a growth medium containing agar, specific for the growth of oomycetes. The devices were placed with the probe in the soil adjacent to carrots during the growing season. After 2 weeks, the devices were collected and transported to the laboratory. All the devices contained a visible pure culture of an oomycetal species in the container. The microorganism present in each device was identified by DNA extraction, amplification by PCR of a specific genomic region and sequencing of such region. The carrots in proximity to some devices showed visual symptoms of cavity spot and a number of species of *Pythium* (*P. violae, P. sylvaticum, P. dissotocum, P. irregulare* and *P. intermedium*) were identified as the disease causative agents.

Example 2: Sampling and subsequent analysis of microorganisms from coir and water in strawberry fields using the sampling devices illustrated in the FIGURE.

Several sampling devices were designed for broad spectrum screening and collection of fungal and fungal-like microorganisms. The devices were placed in the coir bags used for growing strawberries, and in the water collected at the end of each gutter within the strawberry poly-tunnel. The hollow probe and container contained a growth medium containing agar, which was specific for the growth of fungi and oomycetes. After 2 weeks, the devices were collected and transported to the laboratory. The container of the devices contained visible cultures of at least one microorganism, and in some cases, several microorganisms. The microorganisms present in each device were identified by DNA extraction, amplification by PCR of a specific genomic region and sequencing of such region. In this way, a number of microorganism were sampled and identified (e.g. *Phytophthora cactorum, Pythium lutarium, Pythium dissotocum, Botrytis cinerea* and *Chlonostachys rose*), giving the grower useful information about the location of disease pressures and the distribution of beneficial microorganism within the growing system.

The invention claimed is:

1. A sampling device comprising:
   a) a probe which is hollow, has a top end opposing a bottom end, and the bottom end is configured to be inserted into a growth substrate or a water system;
   b) a container positioned at the top end of the probe, and wherein the container is configured to be located above the growth substrate or the water system;
   c) a growth medium for one or more microorganisms, wherein the growth medium coats one or more internal surfaces of both the probe and the container to form a coating;
   d) a cap included as part of the container, wherein the cap is releasable such that the one or more microorganisms are able to be accessed and removed from the container; and
   wherein the growth medium contains a chemoattractant which is a plant pathogen chemoattractant.

2. The sampling device according to claim 1, wherein the growth medium is specific to the one or more microorganisms potentially present in the growth substrate or the water system.

3. The sampling device according to claim 1, wherein components of the growth medium include:
   one or more amino acids or alcohols;
   one or more plant extract or plant compounds selected from phytohormones, plant proteins, plant signaling compounds;
   one or more sugars;
   one or more organic acids;
   one or more phenolics or one or more other proteins selected from casein, pectin, and any derivatives thereof; or
   any combination thereof.

4. The sampling device according to claim 1, wherein the growth medium encourages growth of the one or more microorganisms and directs the one or more microorganisms along the probe, into the container, or both along the probe and into the container.

5. The sampling device according to claim 1, wherein at least part of the one or more internal surfaces of the probe is coated with the coating of the growth medium and a pattern of the growth medium on the one or more internal surfaces of the probe is such that it encourages the one or more microorganisms to move towards the container as it grows on the growth medium.

6. The sampling device according to claim 1, wherein the growth medium comprises antibiotics, nutrients, or both.

7. The sampling device according to claim 1, wherein the growth medium comprises pesticides or fungicides.

8. The sampling device according to claim 1, wherein components of the growth medium in the probe are at a lower concentration than the components of the growth medium in the container.

9. The sampling device according claim 1, wherein the growth medium comprises a buffer which maintains a pH of the growth medium in the probe.

10. The sampling device according to claim 1, wherein the growth medium comprises a buffer in both the probe and the container; and
    wherein the buffer in the growth medium in the container is at a lower concentration than the buffer in the growth medium in the probe.

11. The sampling device according to claim 1, wherein the growth medium contains a gelling agent by which it adheres to an inside of the probe of the sampling device.

12. The sampling device according to claim 1, wherein the probe is from 4 cm to 10 cm long with a cross sectional area of 0.5 cm$^2$ to 5 cm$^2$.

13. The sampling device according to claim 12, wherein the coating of the growth medium on the one or more internal surfaces of the probe has a thickness of 0.1 cm to 1 cm.

14. The sampling device according to claim 1 in which the growth medium contains one or more amino acids, one or more $C_1$ to $C_4$ monohydric alcohols, or mixtures thereof.

15. The sampling device according to claim 1, wherein the growth medium is included in the container such that a disease-causing organism is both attracted to the probe and encouraged to flow up the probe into the container.

16. The sampling device according to claim 1, wherein the coating of the growth medium coats the probe with an increasing thickness towards the container.

17. A sampling device comprising:
   a) a probe which is hollow, has a top end opposing a bottom end, and the bottom end is configured to be inserted into a growth substrate or a water system;
   b) a container positioned at the top end of the probe, and wherein the container is configured to be located above the growth substrate or the water system;
   c) a growth medium for one or more microorganisms, wherein the growth medium coats one or more internal surfaces of both the probe and the container to form a coating;
   d) a cap included as part of the container, wherein the cap is releasable such that the one or more microorganisms are able to be accessed and removed from the container;
   wherein the growth medium contains a chemoattractant which is a plant pathogen chemoattractant;

wherein the coating of the growth medium coats the one or more internal surfaces of the probe with an increasing thickness towards the container; and wherein the growth medium is configured to encourage growth of the one or more microorganisms and direct the one or more microorganisms along the probe, into the container, or both along the probe and the container.

\* \* \* \* \*